(12) United States Patent
Brinkmann et al.

(10) Patent No.: US 11,806,261 B2
(45) Date of Patent: Nov. 7, 2023

(54) IN VIVO ADJUSTMENT MECHANISM AND ASSOCIATED SYSTEMS AND METHODS

(71) Applicant: W. L. Gore & Associates, Inc., Newark, DE (US)

(72) Inventors: John M. Brinkmann, Flagstaff, AZ (US); Paul D. Goodman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 262 days.

(21) Appl. No.: 17/251,028

(22) PCT Filed: Jun. 7, 2019

(86) PCT No.: PCT/US2019/035993
§ 371 (c)(1),
(2) Date: Dec. 10, 2020

(87) PCT Pub. No.: WO2019/241057
PCT Pub. Date: Dec. 19, 2019

(65) Prior Publication Data
US 2021/0169667 A1 Jun. 10, 2021

Related U.S. Application Data

(60) Provisional application No. 62/683,295, filed on Jun. 11, 2018.

(51) Int. Cl.
*A61F 2/93* (2013.01)
(52) U.S. Cl.
CPC .......... *A61F 2/93* (2013.01); *A61F 2250/001* (2013.01); *A61F 2250/0082* (2013.01)

(58) Field of Classification Search
CPC ...... A61F 2/92; A61F 2/93; A61F 2220/0025; A61F 2220/0033; A61F 2250/001; A61F 2250/0018; A61F 2250/0082
See application file for complete search history.

(56) References Cited

U.S. PATENT DOCUMENTS

| | | | | |
|---|---|---|---|---|
| 5,441,515 A | * | 8/1995 | Khosravi | A61F 2/93 623/1.42 |
| 6,033,436 A | | 3/2000 | Steinke et al. | |

(Continued)

FOREIGN PATENT DOCUMENTS

| | | |
|---|---|---|
| DE | 19951148 A1 | 4/2001 |
| WO | 2012/018779 A2 | 2/2012 |

(Continued)

OTHER PUBLICATIONS

International Preliminary Reporton Patentability received for PCT Patent Application No. PCT/US2019/035993, dated Dec. 24, 2020, 7 pages.

(Continued)

*Primary Examiner* — Paul B Prebilic (57) ABSTRACT

A diametric adjustment mechanism for an implantable medical device including a track defining a series of diametric setpoints, including a first diametric setpoint and a second diametric setpoint, a rider engaged with the track such that the rider is selectively movable along the track from the first diametric setpoint to the second diametric setpoint and from the second diametric setpoint to the first diametric setpoint, and a biasing element biasing the rider toward the first diametric setpoint when the rider is at the second diametric setpoint.

16 Claims, 4 Drawing Sheets

(56) References Cited

U.S. PATENT DOCUMENTS

| | | |
|---|---|---|
| 7,842,081 B2 | 11/2010 | Yadin |
| 8,206,433 B2 | 6/2012 | Rucker |
| 8,435,284 B2 | 5/2013 | Eidenschink et al. |
| 2004/0030381 A1 | 2/2004 | Shu |
| 2009/0030501 A1* | 1/2009 | Morris ................ A61F 2/92 |
| | | 623/1.15 |
| 2011/0093060 A1 | 4/2011 | Cartledge et al. |
| 2011/0172692 A1 | 7/2011 | Wu |
| 2016/0250021 A1 | 9/2016 | Fogarty et al. |
| 2018/0125632 A1 | 5/2018 | Cully et al. |

FOREIGN PATENT DOCUMENTS

| | | | |
|---|---|---|---|
| WO | 2016/167002 A1 | 10/2016 | |
| WO | WO-2018156613 A1 * | 8/2018 | ............ A61F 2/04 |

OTHER PUBLICATIONS

International Search Report and Written Opinion received for PCT Patent Application No. PCT/US2019/035993, dated Sep. 12, 2019, 9 pages.

\* cited by examiner

IN VIVO ADJUSTMENT MECHANISM AND ASSOCIATED SYSTEMS AND METHODS

CROSS-REFERENCE TO RELATED APPLICATION

This application is a national phase application of PCT Application No. PCT/US2019/035993, internationally filed on Jun. 7, 2019, which claims the benefit of Provisional Application No. 62/683,295, filed Jun. 11, 2018, both of which are incorporated herein by reference in their entireties for all purposes.

FIELD

The present disclosure relates generally to implantable medical devices, and more specifically to mechanisms for adjusting the diameter of implantable medical devices and associated methods thereof.

BACKGROUND

Implantable medical devices such as stents, stent-grafts, valves, and other intraluminal devices are used in a variety of medical procedures including to maintain, open, or adjust various body passageways or body lumens to maintain, prevent, and/or adjust fluid flow therethrough. Such devices may be implanted in various locations within the body of a patient including in the vascular system, coronary system, urinary tract, and bile ducts, among others.

In some instances, the size of the medical device required may change over time. For example, devices implanted in children may need to be removed and replaced with larger diameter devices as the child grows. In other scenarios, it may be beneficial to implant a larger diameter device and incrementally decrease the diameter, for example, to seal off a defect or slow fluid flow to a certain, afflicted area such as an aneurysm. It may also be beneficial to increase or decrease the size of a body lumen to adjust the rate of fluid flow therethrough such as during dialysis or instances of heart or kidney failure.

The diameters of implantable medical devices are often not easily adjustable or customizable, and many devices do not permit intravenous or percutaneous diametric adjustments. Current practices often require replacement of the device with a new, differently sized device altogether, which may require further operation and/or invasive procedures, causing added risk, stress and discomfort to the patient.

SUMMARY

Various examples relate to mechanisms for adjusting the diameter of a variety of implantable medical devices and methods thereof. In particular, various examples relate to diametric adjustment mechanisms having a track defining a series of diametric setpoints, a rider engaged with the track and movable between the series of diametric setpoints, and a biasing element biasing the rider in a certain direction along the track.

According to one example ("Example 1"), a diametric adjustment mechanism for an implantable medical device includes a track. The track defines a series of diametric setpoints including a first diametric setpoint and a second diametric setpoint. The adjustment mechanism also includes a rider engaged with the track. The rider is selectively movable along the track from the first diametric setpoint to the second diametric setpoint and/or from the second diametric setpoint to the first diametric setpoint. The adjustment mechanism also includes a biasing element biasing the rider toward the first diametric setpoint when the rider is at the second diametric setpoint.

According to another example ("Example 2") further to Example 1, the track defines a stepped path. The first diametric setpoint is at a first step location of the stepped path and the second diametric setpoint is at a second step location of the stepped path.

According to another example ("Example 3") further to any of Examples 1 to 2, the track defines a first adjustment path between the first diametric setpoint and the second diametric setpoint and a return path from the second diametric setpoint and the first diametric setpoint.

According to another example ("Example 4") further to any of Examples 1 to 3, the track defines an intermediate diametric setpoint between the first diametric setpoint and the second diametric setpoint. The rider is engaged with the track such that the rider is selectively movable along the track from the first diametric setpoint to the intermediate diametric setpoint prior to moving to the second diametric setpoint, and from the intermediate diametric setpoint to the second diametric setpoint.

According to another example ("Example 5") further to any of Examples 1 to 4, the biasing element is a collar having elastic properties.

According to another example ("Example 6") further to any of Examples 1 to 5, the track defines a continuous loop.

According to another example ("Example 7") further to any of Examples 1 to 6, the track includes at least one of a groove, a channel, a notch, an indentation, and a rail.

According to another example ("Example 8") further to any of Examples 1 to 7, the biasing element is configured to maintain the rider at the first diametric setpoint until a biasing force of the biasing element is exceeded by an external force to move the rider to the second diametric setpoint. The biasing element maintains the rider at the second diametric setpoint until the biasing force of the biasing element is exceeded by an external force.

According to another example ("Example 9") further to any of Examples 1 to 8, the rider is a projection and the track is a depression slidably receiving the projection.

According to another example ("Example 10"), a medical device includes a tubular implant and the adjustment mechanism of any of Examples 1 to 9. The adjustment mechanism is coupled to the tubular implant. The biasing element of the adjustment mechanism includes a collar formed of a resilient material, the collar being coupled to the tubular implant.

According to another example ("Example 11") further to Example 10, the biasing element overlaps itself to form the collar.

According to another example ("Example 12") further to Example 11, the biasing element includes a first portion and a second portion. The first portion overlaps the second portion to engage the rider with the track.

According to another example ("Example 13"), a method of adjusting the diameter of the medical device of any of Example 1 to 12 includes imparting a first diametric force on the tubular element to move the rider from the first diametric setpoint to the second diametric setpoint. The method also includes imparting a second diametric force on the tubular element to move the rider from the second diametric setpoint to the first diametric setpoint.

According to another example ("Example 14") further to Example 13, the diametric force is an expanding force imparted on an interior of the tubular implant with a balloon catheter.

According to another example ("Example 15") further to any of Examples 13 to 14, moving the rider from the first diametric setpoint to the second diametric setpoint adjusts the diameter of the medical device from a first diameter to a second diameter. Moving the rider from the second diametric setpoint to the first diametric setpoint adjusts the diameter of the medical device from the second diameter to the first diameter.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Various aspects of the present disclosure relate to adjustment mechanisms for adjusting diameters of implantable medical devices. Examples of implantable medical devices can include stents, stent-grafts, valves, and devices for occlusion and/or anastomosis, among others. In certain examples, the implantable medical devices may be configured to adjust (e.g., increase and/or decrease) the size of a particular artificial or natural body lumen, passageway, and/or conduit to promote, restrict, or otherwise adjust fluid flow therethrough. For reference, the term "lumen" should be read broadly to include any of a variety of passages, such as those associated with the vasculature, biliary tract, urinary tract, lymph system, reproductive system, gastrointestinal system, or others.

In certain instances, it may be beneficial to adjust the diameter of implantable medical devices after implantation inside the body of a patient. For example, in certain applications where the size of the body lumen increases or decreases over time, it may be beneficial to increase and/or decrease the diameter of the device to fit the changing size of the body lumen. In other instances, it may be beneficial to gradually reduce or restrict the flow of blood to a certain area, such as slowing blood flow to an aneurysm, adjusting urine flow during and/or after dialysis, and restricting and/or decreasing blood flow during heart or kidney failure.

In the above examples, it may also be beneficial to be able to adjust the implantable medical devices without additional, invasive procedures. Procedures such as these can impart added stress and discomfort on the patient. Therefore, a device that reduces potential, additional burden on the patient and/or medical provider would be desirable.

Figure 1:
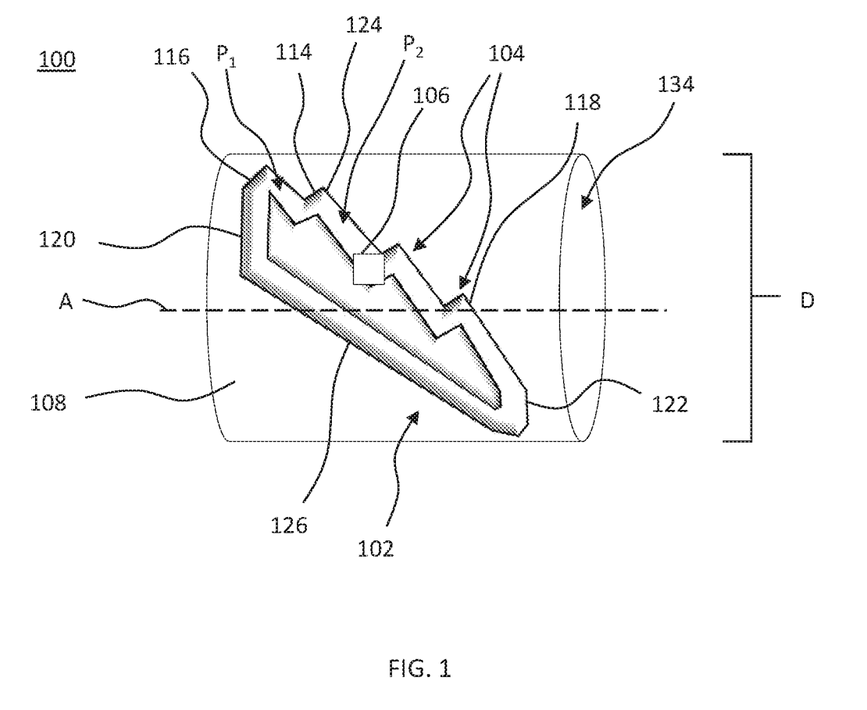
FIG. 1 is a side view of a diametric adjustment mechanism for an implantable medical device, according to some embodiments.
Figure 3A:
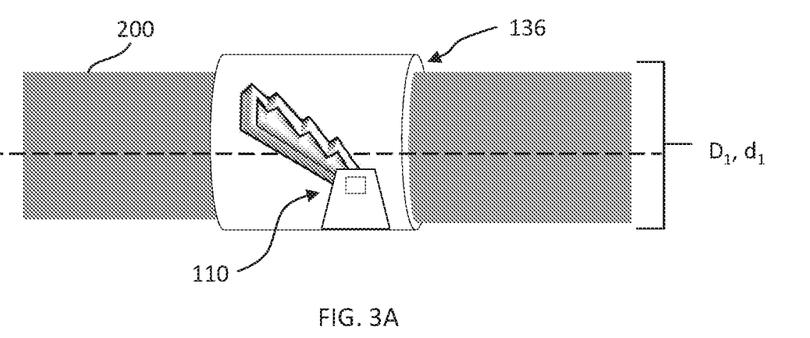
FIG. 3A is a side view of a diametric adjustment mechanism coupled to an implantable medical device at a first diametric setpoint, according to some embodiments.

FIG. 1 shows a diametric adjustment mechanism for an implantable medical device, according to some embodiments. The diametric adjustment mechanism 100 includes a track 102 defining a series of diametric setpoints 104, a rider 106 engaged with the track 102 and selectively movable along the track 102 between the series of diametric setpoints 104, and a biasing element 108 to promote movement of the rider 106 in a certain direction along the track 102. In some embodiments, the diametric adjustment mechanism 100, also referred to herein simply as the adjustment mechanism 100, is coupled to an implantable medical device 200 (FIG. 3). The series of diametric setpoints 104 includes at least two setpoints, for example, a first diametric setpoint 110 (FIG. 3A) and a second diametric setpoint 112 (FIG. 3C), but may include more setpoints as desired. As the rider 106 moves along the track 102 between the series of diametric setpoints 104, the diameter D of the adjustment mechanism 100 is either increased or decreased depending on the direction in which the rider 106 moves along the track 102. For example, the rider 106 could move in a clockwise direction around the track 102 or in a counter-clockwise direction around the track 102 depending on the configuration of the track 102. As the diameter D of the adjustment mechanism 100 is increased or decreased, the diameter d (FIG. 3A) of the implantable medical device 200 also increases or decreases.

In some embodiments, the series of diametric setpoints 104 correspond to a series of stop points spaced along the track 102 configured to keep the rider 106 at a certain location along the track 102 until a biasing force imparted by the biasing element 108 on the rider 106 is overcome. In other words, each of the stop points keep the adjustment mechanism 100 at a respective, desired diameter D until the biasing force is overcome and the rider 106 moves to the subsequent stop point. The biasing force can be overcome by application of a diametric force (e.g., a radial force applied in a radially outward direction from the longitudinal axis A of the adjustment mechanism 100), a magnetic force (e.g., applied externally through the skin of a patient), or any other applied force that exceeds the biasing force and to cause the rider 106 to move along the series of diametric setpoints 104. In some examples, the diametric force is an expansion force imparted on an interior of the implantable medical device 200 using a balloon catheter, although other methods of imparting an expansion force upon the adjustment mechanism 100 are also contemplated.

In various embodiments, the series of diametric setpoints 104 can be any of a series of notches, steps, grooves, bends, curves, crooks, or any other configuration capable of keeping the rider 106 at a certain location along the track 102. In some examples, the series of diametric setpoints 104 may include portions that are flat, upwardly angled, or otherwise inflected as compared to the rest of the track 102 so that the rider 106 may sit, rest, or lodge at the respective one of the series of setpoints 104 until the biasing force is overcome, as shown in FIG. 1.

In some embodiments, the series of diametric setpoints 104 includes a first diametric setpoint 110 and a second diametric setpoint 112. The first diametric setpoint 110 corresponds to a first diameter $D_1$ of the adjustment mechanism 100 and the second diametric setpoint 112 corresponds to a second diameter $D_2$ of the adjustment mechanism 100. Thus, moving the rider 106 between the first diametric setpoint 110 and the second diametric setpoint 112 causes the diametric adjustment mechanism 100 to increase and/or decrease from the first diameter $D_1$ to the second diameter $D_2$ and, in turn, causes the implantable medical device 200 to also increase or decrease from a first device diameter $d_1$ to a second device diameter $d_2$.

The track 102 can include additional setpoints, as desired, for adjusting the diameter D of the adjustment mechanism 100. For example, the track 102 can include an intermediate diametric setpoint 124 located between the first diametric setpoint 110 and the second diametric setpoint 112. Similar to the first and second diametric setpoints 110, 112, the intermediate diametric setpoint 124 corresponds to an intermediate diameter $D_I$ of the diametric adjustment mechanism 100, the intermediate diameter $D_I$ being between the first diameter $D_1$ and the second diameter $D_2$. Additional diametric setpoints may allow for incremental adjustment of the adjustment mechanism 100 and/or the implantable medical device 200 between any number of diameters as desired. For example, in certain instances, a larger number of smaller, incremental diametric adjustments may be necessary or beneficial where, in other instances, fewer, larger adjustments may be desired.

In some embodiments, the track 102 defines a stepped path 114, as shown in FIG. 1, with each of the series of diametric setpoints 104 spaced along the stepped path 114. In some embodiments, the first diametric setpoint 110 is located at a first step location 116 along the stepped path 114 and the second diametric setpoint 112 is located at a second step location 118 along the stepped path 114. As discussed above, moving the rider 106 between the first diametric setpoint 110 (e.g., the first step location 116) and the second diametric setpoint 112 (e.g., the second step location 118) causes the adjustment mechanism 100 to increase and/or decrease from the first diameter $D_1$ to the second diameter $D_2$. In some embodiments, the first step location 116 may be near a first end 120 of the track 102 and the second step location 118 may be near a second end 122 of the track 102. However, the first and second step locations 116, 118 can be located anywhere along the track 102 as desired.

In some embodiments, the track 102 defines a first adjustment path $P_1$. The first adjustment path $P_1$ may be, for example, between the first diametric setpoint 116 and the second diametric setpoint 118. For example, the rider 106 can move along the first adjustment path $P_1$ to adjust the adjustment mechanism 100 between the first diameter $D_1$ and the second diameter $D_2$. In some embodiments, the first adjustment path $P_1$ may also be between the first diametric setpoint 116 and the intermediate diametric setpoint 124. For example, the rider 106 can move along the first adjustment path $P_1$ from the first diametric setpoint 116 to the intermediate diametric setpoint 124 prior to moving to the second diametric setpoint 118.

In some embodiments, the track 102 also defines a second adjustment path $P_2$. For example, after moving from the first diametric setpoint 116 to the intermediate diametric setpoint 124, the rider 106 may then move along the second adjustment path $P_2$ from the intermediate diametric setpoint 124 to the second diametric setpoint 118. In various embodiments, the track 102 may define a third adjustment path, a fourth adjustment path, or any number of adjustment paths between each setpoint of the series of diametric setpoints 104 as desired.

Although the adjustment mechanism 100 is described above and shown in FIG. 1 to decrease in diameter as the rider 106 moves along the first adjustment path $P_1$ and the second adjustment path $P_2$, the mechanism 100 can also be configured to increase in diameter as the rider 106 moves along the first and second adjustment paths $P_1$, $P_2$. For example, as the rider 106 moves along the first adjustment path $P_1$ from the first diametric setpoint 116 to the intermediate diametric setpoint 124, the diameter D of the adjustment mechanism 100 may increase (i.e., from a smaller diameter to a larger diameter), and may further increase as the rider 106 moves along the second adjustment path $P_2$ from the intermediate setpoint 124 to the second diametric setpoint 118.

In some embodiments, the track also defines a return path 126 between the second diametric setpoint 112 and the first diametric setpoint 110. The return path 126 allows for diametric adjustment of the adjustment mechanism 100 from the second diameter $D_2$ to the first diameter $D_1$. In some embodiments, the return path 126 may be located adjacent and substantially parallel to the stepped path 114. In some embodiments, the return path 126 may be substantially straight such that the rider 106 can move continuously and uninterrupted from the second diametric setpoint 112 to the first diametric setpoint 110. In some embodiments, the return path 126 allows for return of the rider 106 to its original location (e.g., the first step location 116) so that in use the rider 106 remains continually engaged with the track 102.

In some embodiments, the track 102 may define a continuous loop, as shown in FIG. 1. This allows the rider 106 to move along the track 102 (e.g., between the series of diametric setpoints 104) without disengaging from the track 102. For example, the rider 106 can move along the stepped path 114 from the first diametric setpoint 110 to the second diametric setpoint 112 and then move along the return path 126 from the second diametric setpoint 112 to the first diametric setpoint 110 without disengaging from the track 102.

In various examples, the rider 106 and the track 102 are complementary features that are configured to remain slidably coupled during diametric adjustment. In some embodiments, the rider 106 may be a projection, groove, or other feature capable of slidably engaging with the track 102. The track 102 may define a depression or relief feature capable of receiving the rider 106, or a raised rail or other feature on which the rider 106 traverses. For example, the track 102 can include at least one of a groove, a channel, a notch, an indentation, a rail, or any other feature capable of receiving or otherwise engaging with the rider 106.

In some embodiments, the diametric adjustment mechanism 100 includes a biasing element 108, as shown in FIG. 1. As discussed above, the biasing element 108 promotes movement of the rider in a certain, desired direction along the track 102. For example, the biasing element 108 may bias or promote movement of the rider 106 toward the second diametric setpoint 112 when the rider 106 is at the first diametric setpoint 110, or toward the first diametric setpoint 110 when the rider 106 is at the second diametric setpoint 112. In some embodiments, the biasing element 108 is configured to maintain the rider 106 at the first diametric setpoint 110 until the biasing force of the biasing element 108 is exceeded by the diametric force (i.e., from the catheter balloon, the magnet, or a bodily function such as, for example, a heartbeat) to move the rider 106 to the second diametric setpoint 112, at which movement of the rider 106 is halted until the biasing force of the biasing element 108 is again exceeded by the diametric force.

Figure 2:
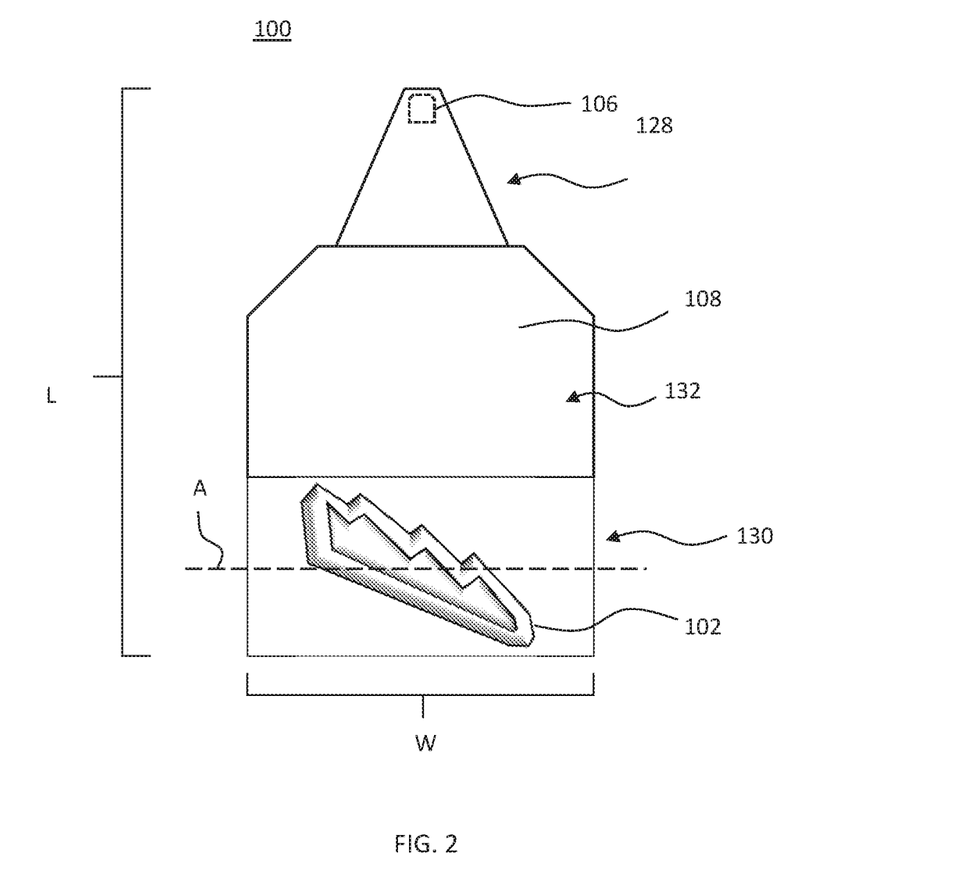
FIG. 2 is a top view of a diametric adjustment mechanism for an implantable medical device, according to some embodiments.

FIG. 2 shows the diametric adjustment mechanism 100 coupled to the biasing element 108, according to some embodiments. In some embodiments, the biasing element 108 is formed of a resilient material capable of imparting a bias on the rider 106, as discussed above. In other words, the biasing element 108 promotes movement of the rider 106 in a certain direction along the track 102. For example, where the capability to incrementally adjust an increasing diameter is desired, then the biasing element 108 may be configured to bias the adjustment mechanism 100 toward the smaller diametric setpoint. In turn, wherein the capability to incrementally adjust from a larger diameter to a smaller diameter is desired, then the biasing element 108 may be configured to bias the adjustment mechanism 100 toward the smaller diametric setpoint (e.g., biasing the rider 106 in a direction along the track 102 from the first diametric setpoint 110 toward the second diametric setpoint 112). In some embodiments, the biasing element 108 is formed of a substantially flat sheet of material capable of overlapping itself to form a generally tubular or cylindrical shape, as is shown in FIG. 1. In some embodiments, the biasing element 108 may include a length L extending from a first portion 128 to a second portion 130, and a width W, the width W being a dimension perpendicular to the length L. The biasing element 108 also includes an outer surface 132, an inner surface 134 (FIG. 1), and a longitudinal axis A. In some embodiments, the track 102 is coupled to the outer surface 132, near the second portion 130, of the biasing element 108 and the rider 106 is coupled to the inner surface 134, near the first portion 128, of the biasing element 108 such that, when the biasing element 108 is folded over itself and overlaps (e.g., the first portion 128 overlaps the second portion 130), the rider 106 engages the track 102 so that the rider 106 is slidably coupled to the track 102.

Figure 3B:
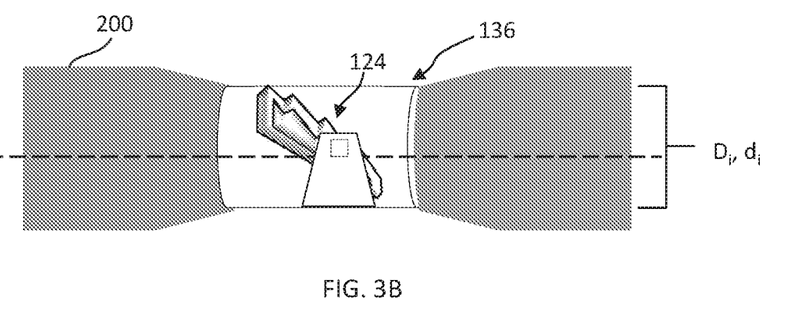
FIG. 3B is a side view of a diametric adjustment mechanism coupled to an implantable medical device at an intermediate diametric setpoint, according to some embodiments.
Figure 3C:
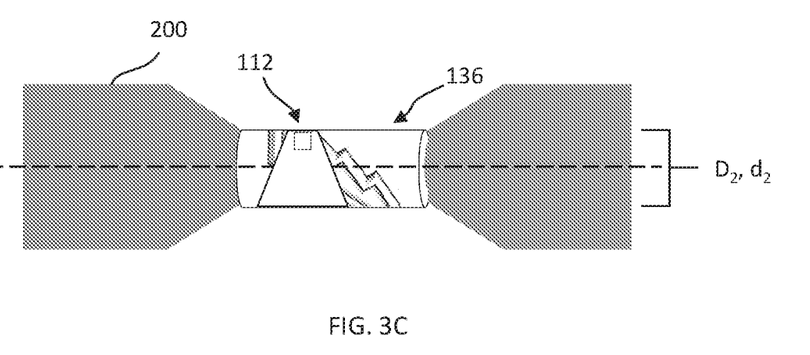
FIG. 3C is a side view of a diametric adjustment mechanism coupled to an implantable medical device at a second diametric setpoint, according to some embodiments.

FIGS. 3A to 3C show the adjustment mechanism 100 coupled to an implantable medical device 200 in the form of a tubular implant. As shown, the adjustment mechanism 100 can be coupled to the implantable medical device 200 such that, when the adjustment mechanism 100 changes from the first diameter $D_1$ to the second diameter $D_2$, the implantable medical device 200 also changes from the first device diameter $d_1$ to the second device diameter $d_2$. As discussed above, examples of implantable medical devices 200 in the form of tubular implants may include stents and stent-grafts, among other tubular, cylindrically-shaped devices (e.g., heart valves, vascular filters, anastomosis devices, occluders, and others).

FIG. 3A shows the diametric adjustment mechanism 100 coupled to the implantable medical device 200 in an expanded configuration or, in other words, at the first diameter $D_1$. As shown, the rider 106 is located at the first diametric setpoint 110 (e.g., at the first step location 116). The first diametric setpoint 110 corresponds to the first diameter $D_1$ of the adjustment mechanism 100 and the first device diameter $d_1$ of the implantable medical device 200.

As shown, the biasing element 108 can be a cylindrical member 136, also described as a collar 136, configured to surround an outer surface or a portion of the exterior surface of the implantable medical device 200. In some embodiments, the collar 136 has elastic properties that impart the bias on the adjustment mechanism 100. As discussed above, when the biasing force is overcome by the diametric force, the rider 106 moves, for example, from the first diametric setpoint 110 to the second diametric setpoint 112, adjusting the diameters of the adjustment mechanism 100 and implantable medical device 200 as described above.

FIG. 3B shows the adjustment mechanism 100 at the intermediate diameter $D_i$. The rider 106 is located at the intermediate diametric setpoint 124. As discussed above, the intermediate diametric setpoint 124 corresponds to an intermediate diameter $D_i$ of the diametric adjustment mechanism 100 and an intermediate device diameter $d_i$ of the implantable medical device 200. As shown, movement of the rider 106 along the track 102 or, in some examples, along the stepped path 114, facilitates adjustment of the implantable medical device 200 from the first device diameter $d_1$ to the intermediate device diameter $d_i$.

FIG. 3C shows the adjustment mechanism 100 in a compressed configuration or, in other words, at the second diameter $D_2$. As shown, the rider 106 is located at the second diametric setpoint 112 (e.g., at the second step location 118). The second diametric setpoint 112 corresponds to the second diameter $D_2$ of the adjustment mechanism 100 and the second device diameter $d_2$ of the implantable medical device 200.

In some embodiments, a method of adjusting the diameter d of the implantable medical device 200 includes imparting a first diametric force on the diametric adjustment mechanism 100. The first diametric force moves the rider 106 from the first diametric setpoint 110 to the second diametric setpoint 112 along the stepped path 114 according to a first configuration as can be seen in FIGS. 3A to 3C (configured to transition from a larger diameter to a smaller diameter under the first diametric force, which is a compressive force) or according to a second configuration as can be seen in FIGS. 4A to 4C (configured to transition from a smaller diameter to a larger diameter under the first diametric force $F_{D1}$, which is an expansion force).

According to FIGS. 3A to 3C, in some embodiments, the first diametric force may be a constrictive or compressive force configured to alter the diameter d of the implantable medical device 200. In some examples, the diametric force is imparted by a manual force applied through the skin (e.g., by hand) or a force applied using one or more transcatheter devices (e.g., a balloon catheter or other device capable of diametric adjustment). The diametric force may also be applied (whether internally or externally) as a magnetic force that interacts with the rider 106 and "forces" or moves the rider 106 along the track 102 between any setpoints of the series of diametric setpoints 104 as desired. The method also includes imparting a second diametric force on the diametric adjustment mechanism 100. In some examples, the second diametric force releases the rider 106 from the second diametric setpoint 112 and allows movement of the rider 106 from the second diametric setpoint 112 to the first diametric setpoint 110 along the return path 126 (e.g., as a result of the biasing force).

Figure 4A:
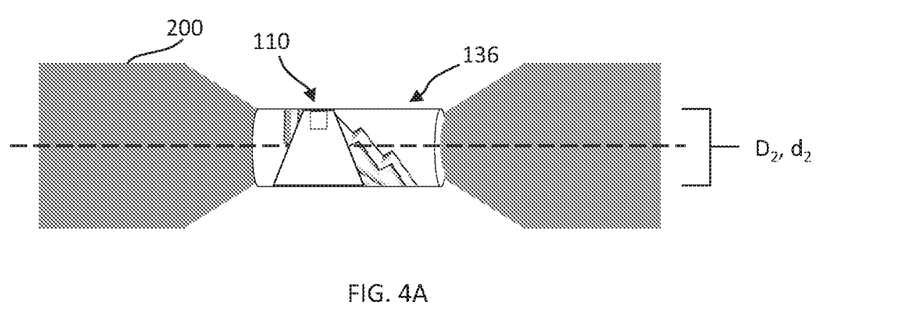
FIG. 4A is a side view of a diametric adjustment mechanism coupled to an implantable medical device at a first diametric setpoint, according to some embodiments.
Figure 4B:
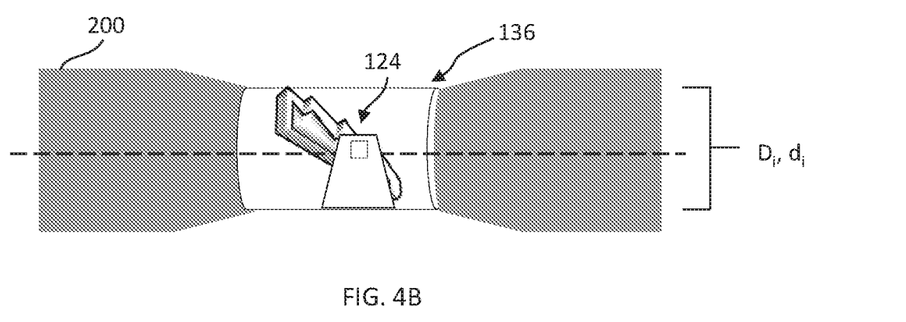
FIG. 4B is a side view of a diametric adjustment mechanism coupled to an implantable medical device at an intermediate diametric setpoint, according to some embodiments.
Figure 4C:
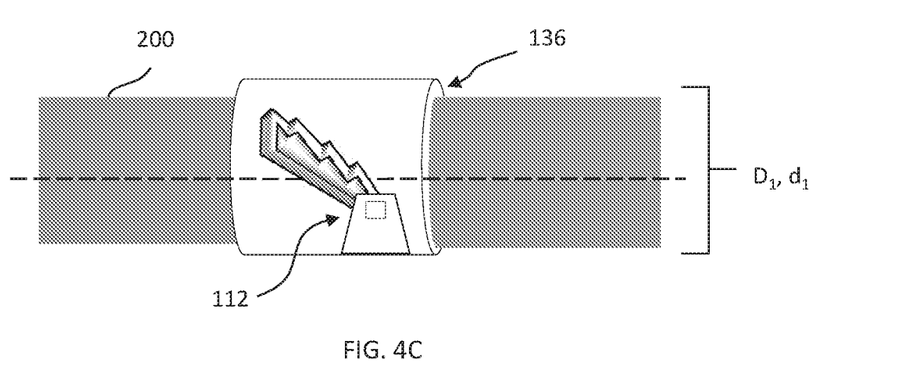
FIG. 4C is a side view of a diametric adjustment mechanism coupled to an implantable medical device at a second diametric setpoint, according to some embodiments.

As shown in FIGS. 4A to 4C, in some embodiments, the first diametric force is an expanding force. The expanding force may be imparted on an interior of the implantable medical device 200 in a variety of ways such as with a balloon catheter, as discussed above.

FIGS. 4A to 4C show the adjustment mechanism 100 and implantable medical device 200 as an incremental expansion force is applied. As shown in FIG. 4A, the rider 106 is positioned at the first diametric setpoint 110 and the implantable medical device 200 is at the second (e.g., reduced) device diameter $d_2$. FIG. 4B shows the adjustment mechanism 100 after a first diametric force has been applied. As shown, the rider 106 is positioned at the intermediate diametric setpoint 124 and the implantable medical device 200 is at the intermediate device diameter $d_1$. FIG. 4C shows the adjustment mechanism 100 after a second diametric force has been applied. The rider 106 is positioned at the second diametric setpoint 112 and the implantable medical device 200 is at the first (e.g., expanded) device diameter $d_1$.

The first and second diametric forces and are described above as both compressive and expansion forces, the first and second diametric force and can be any of a variety of forces capable of overcoming the biasing force and moving the rider 106 along the track 102 from the first diametric setpoint 110 to the second diametric setpoint 112 and vice versa. In some examples, the diametric force is imparted by a manual force applied through the skin (e.g., by hand) or a force applied using one or more transcatheter devices (e.g., a balloon catheter or other device capable of diametric adjustment). The diametric force may also be applied (whether internally or externally) as a magnetic force that interacts with the rider 106 and "forces" or moves the rider 106 along the track 102 from the first diametric setpoint 110 to the second diametric setpoint 112, from the second diametric setpoint 112 to the first diametric setpoint 110, and/or between any setpoints of the series of diametric setpoints 104 as desired. For example, the rider 106 optionally includes a ferromagnetic material upon which an internal or external magnet may act. It should be understood that any other types of diametric forces FD may be used, as desired, to impart an applied force on the rider 106 and overcome the biasing force to move the rider 106 along the track 102.

The adjustment mechanism 100 is optionally employed in a variety of applications. For example, the adjustment mechanism 100 is optionally employed to control flow through an intrahepatic portosystemic shunt device (e.g., in association with devices such as W.L. Gore & Associates Inc.'s product sold under the trade name "GORE® VIA-TORR® TIPS Endoprosthesis." In other examples, the adjustment mechanism 100 is employed in an arteriovenous access application (e.g., to control flow through a fistula or graft, for example). In still further examples, the adjustment mechanism 100 is employed to control flow through a prosthetic valve (e.g., heart valve). In still further examples, the adjustment mechanism is employed to control flow in an aorta of a patient to control flow into the renal arteries of the patient (e.g., by controlling a diameter of a portion of an aortic stent graft). Although a few examples are provided, it should be understood that any of a variety of applications are contemplated. Methods of using the adjustment mechanism include a one-time adjustment, multiple adjustments, and adjustments of any frequency or periodicity (e.g., an adjustment per minute, hour, day, week, year, or per every heart beat).

In some examples, the adjustment mechanism 100 may be configured to adjust the diameter of a medical device with each of the patient's heartbeats. For example, the adjustment mechanism 100 may have many small diametric setpoints that each require a small biasing force to adjust. Therefore, with each heartbeat, the mechanism 100 may incrementally increase in diameter until reaching its full diameter, at which point the mechanism 100 may reset to its minimum diameter and repeat the cycle. The mechanism 100 may also be configured to incrementally decrease in diameter until reaching its minimum diameter, at which point the mechanism 100 may reset to its maximum diameter and repeat. Such continuous increasing or decreasing of the adjustment mechanism 100 may prevent the patient's body from adjusting to a new pressure, flow, or other property created by the presence of the adjustment mechanism 100.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

What is claimed is:

1. A diametric adjustment mechanism for an implantable medical device, the diametric adjustment mechanism comprising:
   a track defining a series of diametric setpoints including a first diametric setpoint and a second diametric setpoint, an adjustment path defined from the first diametric setpoint to the second diametric setpoint, and a return path defined from the second diametric setpoint to the first diametric setpoint, the return path being adjacent to and separate from the adjustment path;
   a rider engaged with the track such that the rider is selectively movable along the track from the first diametric setpoint to the second diametric setpoint, and from the second diametric setpoint to the first diametric setpoint; and
   a collar that is coupled between the rider and the track, the collar having elastic properties such that the collar biases the rider toward the first diametric setpoint when the rider is at the second diametric setpoint.

2. The adjustment mechanism of claim 1, wherein the adjustment path includes a stepped path.

3. The adjustment mechanism of claim 1, wherein the track defines an intermediate diametric setpoint between the first diametric setpoint and the second diametric setpoint, the rider being engaged with the track such that the rider is selectively movable along the track from the first diametric setpoint to the intermediate diametric setpoint prior to moving to the second diametric setpoint, and from the intermediate diametric setpoint to the second diametric setpoint.

4. The adjustment mechanism of claim 1, wherein the track defines a continuous loop.

5. The adjustment mechanism of claim 1, wherein the track includes at least one of a groove, a channel, a notch, an indentation, or a rail.

6. The adjustment mechanism of claim 1, wherein the collar is configured to maintain the rider at the first diametric setpoint until a biasing force of the collar is exceeded by an external force to move the rider to the second diametric setpoint, at which the collar maintains the rider until the biasing force of the collar is exceeded by an external force.

7. The adjustment mechanism of claim 1, wherein the rider is a projection and the track is a depression slidably receiving the projection.

8. A medical device including a tubular implant and the adjustment mechanism of claim 1 coupled to the tubular implant, wherein the collar is formed of a resilient material, the collar being coupled to the tubular implant.

9. The medical device of claim 8, wherein the collar overlaps itself.

10. The medical device of claim 8, wherein the collar includes a first portion and a second portion and wherein the first portion overlaps the second portion to engage the rider with the track.

11. A method of adjusting the diameter of an implantable medical device, the implantable medical device including a diametric adjustment mechanism having a track defining a series of diametric setpoints including an adjustment path between a first diametric setpoint and a second diametric setpoint and a return path between the second diametric setpoint and the first diametric setpoint, the adjustment path being adjacent to and separate from the return path, a rider engaged with the track such that the rider is selectively movable along the adjustment and return paths of the track from the first diametric setpoint to the second diametric setpoint along the adjustment path, and from the second diametric setpoint to the first diametric setpoint along the return path, and a collar biasing the rider toward the first diametric setpoint when the rider is at the second diametric setpoint, the method comprising:

imparting a first diametric force on the tubular element to move the rider from the first diametric setpoint to the second diametric setpoint along the adjustment path; and imparting a second diametric force on the tubular element to move the rider from the second diametric setpoint to the first diametric setpoint along the return path.

12. The method of claim 11, wherein the first diametric force is an expanding force imparted on an interior of the tubular implant with a balloon catheter.

13. The method of claim 11, wherein moving the rider from the first diametric setpoint to the second diametric setpoint adjusts the diameter of the medical device from a first diameter to a second diameter and wherein moving the rider from the second diametric setpoint to the first diametric setpoint adjusts the diameter of the medical device from the second diameter to the first diameter.

14. The adjustment mechanism of claim 1, wherein the return path is substantially straight.

15. The adjustment mechanism of claim 1, wherein the rider remains continuously engaged with the track.

16. The adjustment mechanism of claim 1, wherein the adjustment path and the return path are substantially parallel.

\* \* \* \* \*